United States Patent
Pablos Pérez (10) Patent No.: US 10,398,748 B2
(45) Date of Patent: Sep. 3, 2019

(54) ADDITIVES FOR ANIMAL FEED

(71) Applicant: NOREL ANIMAL NUTRITION USA INC., Pasadena, TX (US)

(72) Inventor: Enrique Pablos Pérez, Madrid (ES)

(73) Assignee: NOREL ANIMAL NUTRITION USA INC., Pasadena, TX (US)

( * ) Notice: Subject to any disclaimer, the term of this patent is extended or adjusted under 35 U.S.C. 154(b) by 0 days.

(21) Appl. No.: 15/809,338

(22) Filed: Nov. 10, 2017

(65) Prior Publication Data

US 2018/0085418 A1    Mar. 29, 2018

Related U.S. Application Data

(62) Division of application No. 13/980,469, filed as application No. PCT/ES2012/070029 on Jan. 20, 2012, now abandoned.

(30) Foreign Application Priority Data

Jan. 21, 2011    (ES) .................................. 201130070

(51) Int. Cl.
| | |
|---|---|
| A61K 36/906 | (2006.01) |
| A61K 36/67 | (2006.01) |
| A61K 9/00 | (2006.01) |
| A61K 36/9068 | (2006.01) |
| A61K 31/19 | (2006.01) |
| A61K 31/20 | (2006.01) |
| A61K 31/4525 | (2006.01) |
| A61K 31/05 | (2006.01) |
| A61K 31/11 | (2006.01) |
| A23K 20/105 | (2016.01) |
| A23K 20/158 | (2016.01) |
| A23K 20/10 | (2016.01) |
| A23K 50/00 | (2016.01) |
| A23K 50/75 | (2016.01) |

(52) U.S. Cl.
CPC .......... *A61K 36/9068* (2013.01); *A23K 20/10* (2016.05); *A23K 20/105* (2016.05); *A23K 20/158* (2016.05); *A23K 50/00* (2016.05); *A23K 50/75* (2016.05); *A61K 9/00* (2013.01); *A61K 31/05* (2013.01); *A61K 31/11* (2013.01); *A61K 31/19* (2013.01); *A61K 31/20* (2013.01); *A61K 31/4525* (2013.01)

(58) Field of Classification Search
None
See application file for complete search history.

(56) References Cited

U.S. PATENT DOCUMENTS

| | | | |
|---|---|---|---|
| 5,741,508 A | 4/1998 | Katsumim | |
| 6,153,246 A | 11/2000 | Gossart | |
| 2002/0182276 A1 | 12/2002 | Wadsworth et al. | |
| 2006/0141010 A1 | 6/2006 | Karl et al. | |
| 2006/0188604 A1 | 8/2006 | Losa | |
| 2007/0116852 A1 | 5/2007 | Schnatmann | |
| 2007/0151480 A1 | 7/2007 | Bloom et al. | |
| 2009/0004308 A1 | 1/2009 | Frehner et al. | |
| 2011/0287104 A1 | 11/2011 | Lorenzon | |
| 2011/0293785 A1 | 12/2011 | Franklin et al. | |
| 2011/0311634 A1 | 12/2011 | Goethals | |
| 2014/0037698 A1 | 2/2014 | Pablos Perez | |

FOREIGN PATENT DOCUMENTS

| | | |
|---|---|---|
| EP | 0619079 A2 | 10/1994 |
| GB | 2466041 A | 6/2010 |
| JP | 06339343 A | 12/1994 |
| JP | 2001017092 A | 1/2001 |
| JP | 2007508804 A | 4/2007 |
| WO | 2004091307 A2 | 10/2004 |
| WO | 2008155536 A1 | 12/2008 |
| WO | 2010108482 A1 | 9/2010 |

OTHER PUBLICATIONS

International Search Report, dated Apr. 24, 2012.
Dipeolu, Olutosin, et al., "Biocatalytic amide reduction using Clostridium sporogenes," Biotechnology Letters, 2001, pp. 1803-1807, vol. 27.
Fernandez-Rubio, C., et al., "Butyric acid-based feed additives help protect broiler chickens from Salmonella Enteritidis infection," Immunology, Health, and Disease, Poultry Science, 2009, pp. 943-948, vol. 88.
Galfi, P., et al.; "Feeding trial in pigs with a diet containing sodium n-butyrate," Acta Vet. Hung., 1990, pp. 3-17, vol. 38—Abstract Only.
Gholamiandehkordi, Ahmad R., et al.; "Quantification of gut lesions in a subclinical necrotic enteritis model," Avian Pathology, 2007, pp. 375-382, vol. 36.
Katoh, K., et al.; "Effects of Acetylcholine and Short-Chain Fatty Acids on Acinar Cells of the Exocrine Pancreas in Sheep," Journal of Physiology, 1984, pp. 479-489, vol. 356.
Leeson, S., et al.; "Effect of Butyric Acid on the Performance and Carcass Yield of Broiler Chickens," Poultry Science, 2005, pp. 1418-1422, vol. 84.
Van Immerseel, F., et al.; "Microencapsulated Short-Chain Fatty Acids in Feed Modify Colonization and Invasion Early After Infection with Salmonella Enteritidis in Young Chickens," Poultry Science, 2004, pp. 69-74, vol. 83.

(Continued)

*Primary Examiner* — Robert T. Crow
*Assistant Examiner* — John P Nguyen
(74) *Attorney, Agent, or Firm* — Tristan A. Fuierer; Olive Law Group, PLLC (57) ABSTRACT

The present invention relates to the combination of organic acid salts with at least one active ingredient of plant origin, preferably essential oils, partially protected with vegetable fats and/or oils, which prevent these active ingredients from being digested by stomach enzymes during the digestive process. The sodium salts of short-chain acids, preferably salts of butyric, acid are preferred. The preferred essential oils are ginger, piperine, oregano, garlic, thymol, carvacrol, cinnamaldehyde and/or any combinations thereof. The combination of organic acid salts and the essential oils protected with vegetable fats and/or oils, are used as powerful promoters or stimulants for animal growth, as organic bactericides against pathogenic bacteria present in said animals and as modulators of immune response thereof.

11 Claims, 5 Drawing Sheets

Specification includes a Sequence Listing.

(56) References Cited

OTHER PUBLICATIONS

Sano, H., et al.; "Plasma insulin and glucagon responses to acute challenges of acetate, propionate, n-butyrate and glucose in growing gilts ( Sus scrofa)" Comp. Biochem. Physiol., 1995, pp. 375-378, vol. 110A.
Cardoso, "Administração oral de piperina em frangos de corte," Ciência Rural, vol. 39, No. 5, pp. 1521-1526, 2009.
English translation of "Administração oral de piperina em frangos de corte," obtained from Google on Feb. 21, 2017.
English translation of WO2010108482 obtained from EPO on Oct. 26, 2015.
Hammer, K.A., et al.; "Antimicrobial activity of essential oils and other plant extracts," Journal of Applied Microbiology, 1999, pp. 985-990, vol. 86.
Windisch, W., et al.; "Use of phytogenic products as feed additives for swine and poultry," J. Anim. Sci. 2008, pp. E140-E148, vol. 86.
Supplementary European Search Report, dated Nov. 11, 2016.
Japanese Office Action, dated Mar. 7, 2016.
Mexican Office Action, dated Jul. 14, 2016.

ADDITIVES FOR ANIMAL FEED

CROSS-REFERENCE TO RELATED APPLICATIONS

This application is filed under the provisions of 35 U.S.C. § 111(a) and is a continuation of U.S. patent application Ser. No. 13/980,469 filed on Oct. 3, 2013, and entitled "ADDITIVES FOR ANIMAL FEED" in the name of Enrique PABLOS PÉREZ, et al., which claims the priority of International Patent Application No. PCT/ES2012/070029 filed on 20 Jan. 2012, which claims priority of Spanish Patent Application No. 201130070 filed on 21 Jan. 2011, all of which are hereby incorporated by reference herein in their entirety.

FIELD OF THE INVENTION

The present invention refers to additives for animal feed based on organic acid salts combined with active ingredients of plant origin together coated with vegetable fats and/or oils. These organic acid salts are used as promoters or stimulants of animal growth, modulators of the immune response and as bactericides. Therefore, the present invention is in the field of animal production and more specifically in the fields of animal feed and health.

STATE OF THE ART

The trend in animal feed in Europe in recent years has been the search for a diet, which not only covers the feeding needs of the animals but also reinforces their health and reduces pathological problems without using medicines, to improve production and economic yields of the farmer. One of the ways of controlling the health and immunity of the animal is by means of controlling intestinal flora.

The use of additives has been common practice in animal feeding with the aim of improving production yields, improving health and thus achieving more efficient utilisation of the food. Because of the prohibition of the use of antibiotics as growth promoting substances in the European Union, (directive 1831/2003/CEE), additives have been sought that often demonstrate improved production compared even to the antibiotics themselves (Dipeolu et al., 2005). Various studies carried out in recent years have shown that organic acids are a good alternative. their mode of action lies, on the one hand, in reducing the pH in the stomach, which limits development of pathogens and helps in protein digestion and, on the other hand, in the ability of some of these organic acids to enter bacteria and block their metabolism. In this sense, butyric acid, also known as butanoic acid, has been studied for several years and beneficial effects have been observed in several species: pigs, poultry, ruminants, etc. and even in fish. Together with acetic and propanoic acids, butyric acid belongs to the group of short-chain volatile fatty acids (VFA). It has been demonstrated that short-chain VFA can inhibit growth of the enterobacteriaceae bacterial group (*Salmonella, Escherichia coli*, etc.), (Van Immerseel et al. 2004). This inhibition occurs owing to the fact that the undissociated forms of the volatile fatty acids are able to cross bacterial membranes, interfere in bacterial metabolism and bring about their death. The acid anion also interferes with gene transcription of the bacteria, which prevents them from reproducing and causing infection. Butyric acid has a better diffusion coefficient than other VFAs, so it crosses the bacterial wall more easily than other acids.

Along with the antibacterial effect, butyric acid has additional effects that make it unique: for example, it stimulates pancreatic secretion (Katoh and Tsudo, 1984; Sano et al, 1995), improves electrolyte absorption, reduces the incidence of diarrhoea, increases microvilli regeneration in the intestine and increases their length (Galfi and Bokori 1990, Lesson et al. 2005) while also increasing the area of intestinal absorption giving rise to higher average weight of poultry and to better food conversion. Thus all these studies demonstrate that butyric acid is beneficial for the livestock farmer, both in terms of nutrition and in terms of health.

It should be pointed out that the free form of butyric acid is difficult to handle because of its high corrosivity and volatility. to solve this problem, various presentations of butyric acid have been developed: salts of butyric acid, salts of microencapsulated butyric acid and salts of butyric acid protected in a matrix of vegetable fats and/or oils, which protect part of the active ingredient and achieve slow release of this natural growth promoter, thus ensuring its growth potentiating and bactericidal action in the animal's digestive tract at the same time as providing the highest protected concentration possible, to include the product in a range of slow-release natural growth promoters. This protected acid salt is marketed under the name of Gustor BP-70 (norel, sa, spain); hereinafter in this invention it will be referred to as BP-70.

Partial protection of salts of butyric acid with vegetable oils and/or fats enables sodium butyrate to act effectively throughout the digestive tract of the animal, ensuring that the active ingredient reaches from the initial sections of the digestive tract to the most distal sections, not only acting as a natural growth promoter but also as a modulator of the immune response and a bactericide, reducing the possibility of infection by pathogenic bacteria. the effectiveness of Gustor BP-70 has been demonstrated in areas where the salts of unprotected butyric acid do not act (caecum/faeces) and in areas where these salts, in encapsulated form, have still not been able to act (crop), making it a complete and effective product in the fight against bacterial infections, especially against *Salmonella enteriditis*, in bird nutrition (Fernández-Rubio c et al, 2009).

The function of sodium butyrate as a bactericide has been mainly employed in the treatment of *Salmonella enteritis*, as this is one of the main pathogenic bacteria affecting animals and man. Among the pathogenic bacteria is the bacterium *Clostridium perfringens*, which causes necrotic enteritis as a consequence of the production of various toxins, resulting in extensive necrosis of the intestinal mucosa, mainly affecting chickens, turkeys, ducks and wild birds. *C. perfringens* occurs naturally in the intestine, proliferating under certain circumstances such as, for example, excess undegraded and undigested nutrients that appear more frequently with dietary changes, especially when animals receive poorly balanced diets or containing poor quality raw materials, poor immune response of the gut-associated lymphoid tissue (GALT) due to excess wear of the intestinal epithelium as a consequence of milling the feed, presence of mycotoxins, coccidia, etc., unbalancing of the intestinal microbial flora and other conditions. In 1972, with the release on the market of the coccidiostat Monensin, the appearance of cases of infection by *C. perfringens* appeared to stop but with the trend for removing antibiotics as growth promoters and for the addition of coccidiostats to the feed, there is a growing trend in the reappearance of this disease.

Therefore, to resolve this growing problem of the rise of infectious diseases in animals for fattening to be used for human consumption, and also to improve the growth of these animals, the present invention has developed a new additive for animal feed comprising salts of organic acids, preferably butyric acid, with active ingredients of natural origin, preferably essential oils, together partially coated with vegetable fats and/or oils. This additive is able to inhibit bacterial growth, especially of Gram-positive bacteria and coccidia, and additionally improves the condition of the intestinal epithelium and improves the weight of treated animals. Partial coating of the active ingredients of this feed additive for animals, the salt of an organic acid and essential oils, with fats and/or oils of plant origin protects these active ingredients from digestion in the stomach, but enables them to be active throughout the gastrointestinal tract of animals because through this partial coating of the active ingredients, phases of the product with various amounts of fat (0%-50% fat) can be produced that are digested and therefore released at different points of the gastrointestinal tract of the animals: the part unprotected by fat is released and has effect in the first sections of the gastrointestinal tract, up to the small intestine; the part protected by fat is not released until the fat starts to be digested by the action of pancreatic lipases. Given the slow digestion of the fat, in vitro studies have shown that part of the active ingredient can reach the most distal parts of the gastrointestinal tract, exercising its action there.

The feed additive described in the present invention is also able to potentiate the development of the intestinal epithelium, encouraging the growth of intestinal villi, which as a consequence of the necrotic enteritis induced in the animals described in the examples of the present invention are reduced in number and size. Furthermore, the increase in development of the intestinal epithelium encourages improved absorption of food, thereby causing an increase in growth and fattening of the animals feeding with the additive. The feed additive described in the present invention is also able to reduce the incidence of bacterial diseases such as necrotic enteritis or those caused by *Salmonella enteriditis*, owing to the modulating action of the immune response and its bactericidal action against pathogens including *C. perfringens* and *S. enterica*. The combined use of the organic acid salt and essential vegetable oils together partially coated with vegetable fats and/or oils is able to potentiate the physiological promoter effect of butyrate such as, for example as mentioned above, in the development of intestinal villi, in addition to potentiating its bactericidal effect.

The other preferred active ingredients, to be included in the combination with organic acid salts, are essential oils. The main synergies of essential oils with organic acid salts from a nutritional point of view are their action as stimulators of digestibility, because they encourage the balance and control of microbial flora; they are also important for their action as stimulators of immunity and antimicrobial and antioxidant properties.

Furthermore, in the present invention, the use of the combination of these organic acid salts and essential oils, together protected with oils and/or fats of plant origin, as a feed additive for animals is described, this feed additive acting as a natural growth promoter as well as bactericide and immunomodulator, able to reduce levels of pathogenic bacteria, specifically *C. perfringens* and *S. enterica*, and improving the immune response with which animals are protected from bacterial infections.

DESCRIPTION OF THE INVENTION

Brief Description of the Invention

The present invention describes a new additive for animal feed that acts as a natural promoter of animal growth and comprises organic acid salts combined with active ingredients of natural origin, preferably essential oils. This combination is partially protected from digestion in the stomach by a partial coating of vegetable fats and/or oils. This coating, being partial, does not prevent the action of the mentioned active ingredients throughout the whole intestinal tract, event to the most distal parts.

The term growth promoters or stimulators is given to those additives that form an integral part of animal diet and that perform the function of improving the daily weight gain of animals (DWG), as well as conversion of the ration consumed. In the present invention, growth promoters or stimulators can be administered by different ways, either by injection, in implants or as an additive in the feed of the animals. In the present invention, the effect of growth is measured as an increase in weight.

For the purpose of the present invention, the term organic acid refers to compounds containing one or more carboxylic groups (—COOH) in their formula, proton donors that can have various functional groups such as hydroxyacids, ketoacids, aromatic acids, heterocyclic compounds and also amides and lactones. The organic acids used in the present invention are preferably volatile fatty acids, preferably short-chain, and can be selected from: butyric acid, propionic acid, formic acid, lactic acid, citric acid, lauric acid, capric acid, caprylic acid, caproic acid, acetic acid and others. The proportions of the organic acid in the additive for animal feed described in the present invention may vary between 30% and 70% of the wet weight of the total product; preferably the proportion is 50%.

The salts of the organic acids used in the present invention are preferably the sodium salt, cupric salt, potassium salt, calcium salt and others. The proportions of the organic acid salt in the additive for animal feed described in the present invention may vary between 30% and 70% of the wet weight of the total product; preferably the proportion is 60%.

In the present invention, the use of the sodium salt of butyric acid (sodium butyrate) is preferred, although any of the salts of the acids listed above may be used.

For the purpose of the present invention, the term active ingredient of plant origin refers to any material of plant origin to which appropriate activity can be attributed that is capable of exercising a beneficial effect on the organism to which it is applied. The active ingredients of plant origin used in the present invention are preferably essential oils. For the purposes of the present invention, the term essential oil refers to a volatile organic substance or substances belonging to various classes of compounds, for example hydrocarbons, esters, alcohols, aldehydes, some acids, phenols and their derivatives, lactones, etc., all long-chain products from plant biosynthesis, called plant secondary metabolites. The term essential oil is also applied to similar synthetic substances, prepared from coal tar, and semi-synthetic substances prepared from the natural essential oils. The essential oils used in the present invention can be selected from any of the following list: ginger, piperine, oregano, garlic, thymol, carvacrol, cinnamaldehyde, etc. The proportions of active ingredients of plant origin in the additive for animal feed described in the present invention may vary between 1% and 20% of the wet weight of the total product, preferably the proportion is 10% of the final product.

For the purposes of the present invention, the term vegetable or plant fat and/or oil refers to an organic compound obtained from seeds or other parts of plants that accumulate in the tissues as an energy source. The vegetable fats and/or oils used in the present invention to coat the combination of the organic acid salt and the active ingredients of natural origin, preferably essential oils, can be selected from: palm stearin (the more solid part obtained after fractioning palm oil) and calcium soap of palm oil fatty acids (palm fatty acid distillate, PFAD) (saponification with calcium of the fatty acids). The proportions of these vegetable fats and/or oils coating the organic acid salt and essential oils described in the present invention may vary between 30% and 60% of the wet weight of the total product, preferably the proportion is 30%.

Furthermore, the present invention describes the use of this additive, natural animal growth promoter, in addition to improving productive parameters of animals (for example increasing their weight), as an immune response modulator and as a bactericide, being able to reduce the incidence in these animals of bacterial diseases such as, for example, necrotic enteritis in poultry, and may also be used for other types of bacterial diseases such as, for example: *Salmonella enteritis, Escherichia coli, Campylobacter* spp., etc. and in other animals such as, for example: rabbits, pigs, etc.

For the purposes of the present invention, the term bactericide is defined as any product, agent or substance able to remove of kill bacteria. For the purposes of the present invention, the bactericidal effect or action is measured as macroscopic changes produced in the intestines of animals due to bacterial infection. Also, for the purposes of the present invention, modulation of the immune response is measured as the change in gene expression with respect to control animals not receiving the additive of the invention in their feed, infected or not, of genes that code for the cytokines, preferably IL-1β, IL-2, CD3δγ and TNFSF15.

DESCRIPTION OF THE FIGURES

FIG. 4B shows the relative levels of expression of the genes IL-1β, IL-2, IL-8, IL-10, CD3γδ, LITAF and RNFSF15 in the groups of animals treated with BP-70 or BP-70+ginger (Group D) compared to the uninfected and untreated animal group (Group A). BP-70+ginger+piperine: sodium butyrate (60% of the wet weight) protected with plant fat (30% of the wet weight)+5% ginger+5% piperine. The squared area of the box spans 50% of all measurements, the horizontal line inside the box represents the mean of the sample and the vertical lines represent 50% of the measurements that were outside the values of the box. The asterisks indicate statistical significance with a value of $p<0.05$. The relative levels of gene expression indicate the expression of each gene compared to the levels of expression of each gene in Group A.

FIG. 4C shows the relative levels of expression of the genes IL-1β, IL-2, IL-8, IL-10, CD3γδ, LITAF and RNFSF15 in the groups of animals treated with BP-70 or BP-70+ginger (Group F) compared to the uninfected and untreated animal group (Group A). BP-70+ginger+piperine: sodium butyrate (60% of the wet weight) protected with plant fat (30% of the wet weight)+5% ginger+5% piperine. The squared area of the box spans 50% of all measurements, the horizontal line inside the box represents the mean of the sample and the vertical lines represent 50% of the measurements that were outside the values of the box. The asterisks indicate statistical significance with a value of $p<0.05$. The relative levels of gene expression indicate the expression of each gene compared to the levels of expression of each gene in Group A.

FIG. 5. Relative levels of expression (Y axis) of the gene TNFSF15 in the various treatment groups: BP-70 (Groups C and E) or BP-70+ginger+piperine (Groups D and F), compared to untreated and uninfected animals (Group A). BP-70: sodium butyrate (70% of the wet weight) protected with vegetable oil (30% of the wet weight). BP-70+ginger+piperine: sodium butyrate (60% of the wet weight) protected with plant fat (30% of the wet weight)+5% ginger+5% piperine. Group B: infected animals but not treated; Group C: uninfected animals treated with BP-70: Group D: uninfected animals treated with BP-70+ginger+piperine; Group E: infected animals treated with BP-70; Group F: infected animals treated with BP-70+ginger+piperine. The squared area of the box spans 50% of all measurements, the horizontal line inside the box represents the mean of the sample and the vertical lines represent 50% of the measurements that were outside the values of the box. The asterisks indicate statistical significance with a value of $p<0.05$. The relative levels of gene expression indicate the expression of each gene compared to the levels of expression of each gene in group a.

FIG. 6. Relative levels of expression (Y axis) of the genes IL-1β, IL-2, IL-8, IL-10, CD3γδ, LITAF and RNFSF15 in the group of animals infected and treated with BP-70+ ginger+piperine (Group F) compared to infected and untreated animals (Group B). BP-70+ginger and piperine: sodium butyrate (60% of the wet weight) protected with vegetable fat (30% of the wet weight)+5% ginger+5% piperine. The squared area of the box spans 50% of all measurements, the horizontal line inside the box represents the mean of the sample and the vertical lines represent 50% of the measurements that were outside the values of the box. The asterisks indicate statistical significance with a value of $p<0.05$. The relative levels of gene expression indicate the expression of each gene compared to the levels of expression of each gene in Group B.

FIG. 7. Relative levels of expression (Y axis) of the gene TNFSF15 in the groups of animals infected and treated with BP-70 (Group E) or with BP-70+ginger+piperine (Group F) compared to infected and untreated animals (Group B). BP-70: sodium butyrate (70% of the wet weight) protected with plant oil (30% of the wet weight). BP-70+ginger+ piperine: sodium butyrate (60% of the wet weight) protected with plant fat (30% of the wet weight)+5% ginger+5% piperine. The squared area of the box spans 50% of all measurements, the horizontal line inside the box represents the mean of the sample and the vertical lines represent 50% of the measurements that were outside the values of the box. The asterisks indicate statistical significance with a value of $p<0.05$. The relative levels of gene expression indicate the expression of each gene compared to the levels of expression of each gene in Group B.

DETAILED DESCRIPTION OF THE INVENTION

One of the objects of the present invention refers to additives for animal feed comprising the combination of organic acid salts with at least one active ingredient of plant origin both together partially coated with vegetable oils and/or fats.

In a preferred embodiment, the additives of the invention are characterised in that the organic acids are selected from any of the list: butyric, lactic, citric, lauric, capric, caprylic, caproic, acetic and others, with butyric acid being preferred.

In another preferred embodiment, the additives of the invention are characterised in that the organic acid salts are selected from any of the list: sodium, calcium, cupric and potassium. The proportions of the organic acid salt in the additive for animal feed described in the present invention may vary between 30% and 70% of the wet weight of the final product, preferably the proportion is 60%.

In another preferred embodiment, the additives of the invention are characterised in that the preferred salt is the sodium salt and the preferred organic acid is butyric acid; therefore the sodium salt of butyric acid is in the preferred additive of the invention.

In another preferred embodiment, the additives of the invention are characterised in that the salt of the organic acid is preferably at a concentration of 60% of the wet weight of the final product.

In another preferred embodiment, the additives of the invention are characterised in that the active ingredients of plant origin are preferably essential oils and can be selected from any included in the list: ginger, piperine, oregano, thymol, garlic, carvacrol, cinnamaldehyde and/or any of their combinations, preferably the combination of the essential oils is ginger and piperine.

In another preferred embodiment, the additives of the invention are characterised in that the vegetable active ingredients are preferably in a proportion of between 1% and 20% of the wet weight of the final product, preferably the proportion is 10% of the wet weight of the final product.

In another preferred embodiment, the additives of the invention are characterised in that the combination of essential oils of ginger and piperine is preferably 5% ginger oil and 5% piperine oil.

In another preferred embodiment, the additives of the invention are characterised in that the partial coating of the combination of organic acid salts and active ingredients of plant origin with vegetable oils and/or fats is approximately between 30% and 60% of the wet weight of the final product, preferably the coating is 30%.

In another preferred embodiment, the additives of the invention are characterised in that the vegetable oils and/or fats that partially coat the combination of organic acid salts and active ingredients of plant origin are selected from: palm stearin and the calcium soap of palm fatty acid distillate (PFAD), preferably palm stearin.

In another preferred embodiment, the additives of the invention are characterised in that the salt is preferably the sodium salt of organic butyric acid, the active ingredient of plant origin is preferably composed of the combination of essential oils, preferably the essential oils of ginger and piperine and the coating of vegetable oils and/or fats is preferably palm stearin.

In another preferred embodiment, the additives of the invention are characterised in that the concentration of sodium butyrate is preferably 60%, the concentration of the combination of the essential oils of ginger and piperine is preferably 10% and the coating of palm stearin is preferably 30%.

In another preferred embodiment, the combination of essential oils of ginger and piperine is preferably composed of 5% ginger oil and 5% piperine oil.

Another of the objects described in the present invention refers to the use of the additives described above for animal feed, as promoters of animal growth, preferably of chickens, rabbits and pigs.

Another of the objects described in the present invention refers to the use, in animal feed for breeding animals fed with the additives described above, as modulator of the immune response. In another preferred embodiment, the modulation of the immune response comprises a change in the expression of any of the genes that code for any of the following cytokines: increasing the expression of IL-1β, IL-2, CD3γδ, and/or reducing the expression of TNFSF15.

Another of the objects described in the present invention refers to the use, in animal feed for breeding animals fed with the additives described above, as a bactericide, inhibiting the growth of both Gram-positive bacteria, preferably bacteria of the genus clostridium, more preferably *C. perfringens*, Gram-negative bacteria, preferably bacteria of the Enterobacteriaceae family, more preferably of the genera *salmonella, Escherichia* and *campylobacter* including protozoans such as the case of the protozoans of the Eimeria and Cryptosporidium families.

The purpose of the examples that are described below is to illustrate the present invention but without limiting its scope.

Example 1. Macroscopic and Histological Pathological Examination in Broiler Chickens that were Induced with Necrotic Enteritis and Treated with Various Feed Additives Conventional broiler chickens were used (hybrid Babolna, Babolna, Hungary) that were one day of age when they were distributed to the various treatment groups described in the present invention. Although the examples were carried out in chickens for fattening (poultry farming), the feed additives that potentiate animal growth and with natural bactericidal action, described in the present invention, can be used in any other type of farming such as, for example: pig, rabbit, sheep, cow, etc.

The broiler chickens were fed a conventional diet free of medicines and rich in proteins (25% fishmeal). This feed had no coccidiostats (agents useful in the treatment or prevention of coccidiosis in humans and/or animals). The animals had no restriction to water and were kept in cages at a density of 30 animals/m². The bedding, watering and feeding equipment were previously sterilised in an autoclave. The ambient temperature was initially set at 32±4° C., reducing to 24±4° C. as the animals grew.

To induce necrotic enteritis, these animals were inoculated with the alpha-toxigenic type a strain of *C. perfringens* (ATCC 13124). This strain was gown in Reinforced Clostridial Medium (BD, MD, USA) culture medium at a temperature of 37° C. for 24 hours in anaerobic conditions making use of the Anaerocult A (Merck, Darmstadt, Germany) system. Then these bacterial cultures were centrifuged (3000 g, 10 min., 5° C., Universal centrifuge 320R, Hettich centrifuges) and the pellet obtained was resuspended in a solution of sterile phosphate buffered saline (PBS). The *C. perfringens* titre was 3-4×$10^8$ colony forming units/ml (CFU/ml). Necrotic enteritis only shows clinical signs if predisposition factors are present. Therefore these animals were infected orally with coccidia by vaccination with the live attenuated vaccine Paracox 5® (Ceva-Phylaxia) and with *C. perfringens A.*

Table 1 shows the infection protocol and vaccination used in the present invention. Briefly, the animals were vaccinated against Gumboro disease or infectious bursitis disease (IBD). This is a highly contagious disease in young chickens caused by infectious bursitis disease virus (IBDV) and is characterised by immunosuppression and death of the animals, usually at the age of between 3 to 6 weeks of age. The vaccine against this disease (CEVAC gumbo L®, Ceva-Phylaxia) was administered in water on day 16 to cause a moderate immunosuppression and to induce the animals to be more susceptible to suffering from necrotic enteritis. Next, they were inoculated orally through a nasogastric tube with 2 mL of a suspension of *C. perfringens* (6.8×$10^8$ CFU) three times a day (8:00, 12:00 and 16:00) on days 18, 19, 20 and 21. On day 19, they were also given a dose 10 times higher than normal of the attenuated live vaccine Paracox-5® (Ceva-Phylaxia), to induce infection by coccidia and to predispose the animals to the clinical disease. The Paracox-5® vaccine is an attenuated live vaccine containing sporulated oocysts derived from precocious strains of coccidia that are pathogenic for chickens: Eimeria acervulina, Eimeria brunetti, Eimeria maxima, Eimeria mitis, Eimeria necatrix, Eimeria praecox and Eimeria tenella. Control animals were also treated with vaccines against gumboro disease and with the Paracox-5® vaccine.

TABLE 1

Infection and vaccination protocol

| Age of chickens (days) | 1 | 16 | 17 | 18 | 19 | 20 | 21 |
|---|---|---|---|---|---|---|---|
| Vaccination against Gumboro | | x | | | | | |
| Infection with Clostridium | | | | x | x | x | x |
| Vaccination with Paracox-5 ® (10 times higher dose than normal) | | | | | x | | |

The broiler chickens (n=24) in this present example were divided into three groups (12 animals/group, Table 2). All the birds were treated with vaccines against Gumboro disease and with the Paracox-5® vaccine on the days indicated in Table 1. All the animals of each group were orally infected with *C. perfringens A* (6-8×$10^8$ CFU). The control group of animals were fed the base diet described, without any additive. In contrast, the other group of animals were fed a diet containing a concentration of 1.5 g/kg feed of the additive described in the present invention: sodium butyrate with ginger and piperine, both active ingredients coated in 30% wet weight of vegetable fats, specifically palm stearin. The sodium butyrate used was the composition from Norel, S.A. called BP-70, to which was added essential oils of ginger (CAS 84696-15-1) (5% wet weight) obtained from Ventós S.A. (Barcelona, Spain) and piperine (5% wet weight) obtained from the company Sensient Fragances S.A. (Granada, Spain). BP-70 is composed of 70% of the wet weight of sodium butyrate and 30% of the wet weight of vegetable fats. The 30% of vegetable fats protects approximately 43% of the total sodium butyrate, therefore the product BP-70 can be described as being composed of 30% protected sodium butyrate and 40% unprotected sodium butyrate. The essential oils of ginger and piperine were coated to the same percentages as the sodium butyrate. All the additives for the feed were supplied by Norel, SA, Spain. The body weight of the animals was measured during the experiment on days 1, 4, 7, 10, 14, 18 and 21. All the animals were sacrificed on day 25.

TABLE 2

Experimental design.

| Animal groups | BP-70 + ginger + piperine (g/kg feed) | Paracox-5 ® | Gumboro | *C. perfringens* A |
|---|---|---|---|---|
| A (n = 12) | — | + | + | + |
| B (n = 12) | 1.5 g/kg | + | + | + |

Grupo A = control, Grupo B = BP-70 + ginger + piperine, Group C = essential oils.

FIG. 1 shows that already on day 17, the day before infection with *C. perfringens* A, the group of animals treated with BP-70+ginger+piperine (Group B) showed an increase in body weight compared to the infected control group but not treated with any feed additive (Group A) (p=0.002). Then another body weight analysis was conducted for each of the groups of animals in the study on day 24, one day before their sacrifice. FIG. 2 shows that similarly to the body weight analysis on day 17 (FIG. 1), this analysis demonstrated that the group treated with BP-70+ginger+piperine showed a significantly higher body weight gain than the control animal group that were infected but not treated with any feed additive (p=0.001).

Next, a histopathological analysis was conducted of the samples collected from various organs of each group of animals: liver, spleen and distal jejunum. Fresh samples were immediately submerged in 10% formalin for preservation until they were used in subsequent analyses. Microscopic lesions were classified in accordance with the method of Gholamiandehkordi et al. (2007) with small deviations: 0=negative; 1=inflammation of the intestine; 2=focal necrosis (1.2 cm) or degenerative changes in the mucosa (fatty appearance); 3=irregular necrosis (3-4 cm) and 4=diffuse necrosis. The presence of enteritis (generally histiocytic lymphoma) was also noted.

Figure 1:
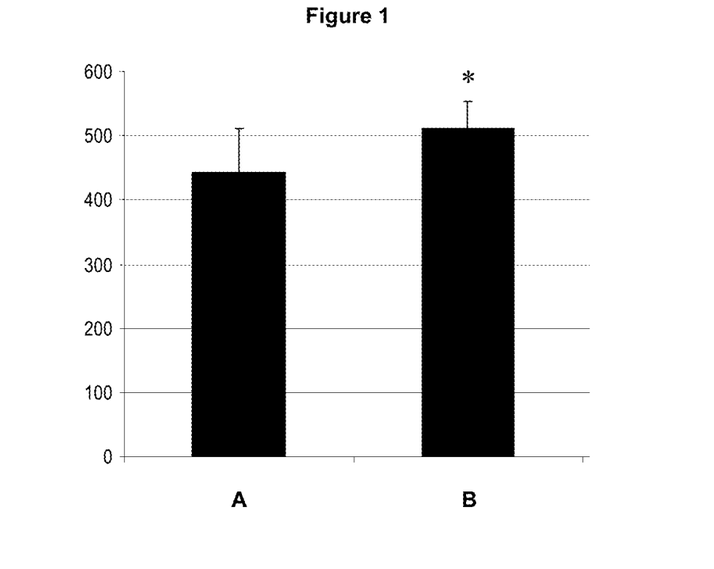
FIG. 1. Weights of animals of the groups A=control and B=BP-70+ginger and piperine on day 17 of the experimental trial. The Y axis shows the weight in grams. The X axis shows the time in days. * indicates statistically significant differences compared to the infected but untreated control group ($p<0.05$). BP-70: sodium butyrate (60% of the wet weight) protected with plant oil (30% of the wet weight). The percentage of ginger and piperine included in the additive was 10% of the wet weight of the total product of each of the essential oils that is 5% ginger and 5% piperine.
Figure 2:
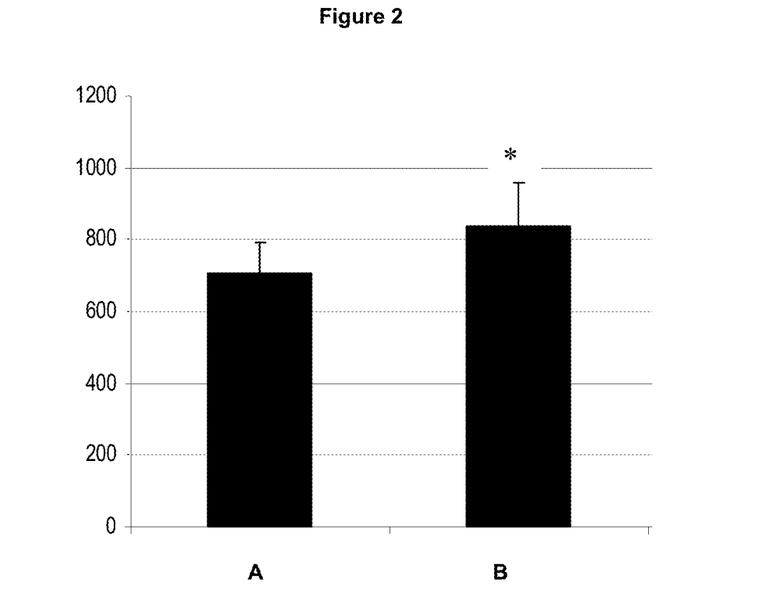
FIG. 2. Weights of animals of the groups A=control and B=BP-70+ginger and piperine on day 24 of the experimental trial. The Y axis shows the weight in grams. The X axis shows the time in days. * indicates statistically significant differences compared to the infected but untreated control group ($p<0.05$). BP-70: sodium butyrate (60% of the wet weight) protected with plant oil (30% of the wet weight). The percentage of ginger and piperine included in the additive was 10% of the wet weight of the total product of each of the essential oils, that is 5% ginger and 5% piperine.
Figure 3:
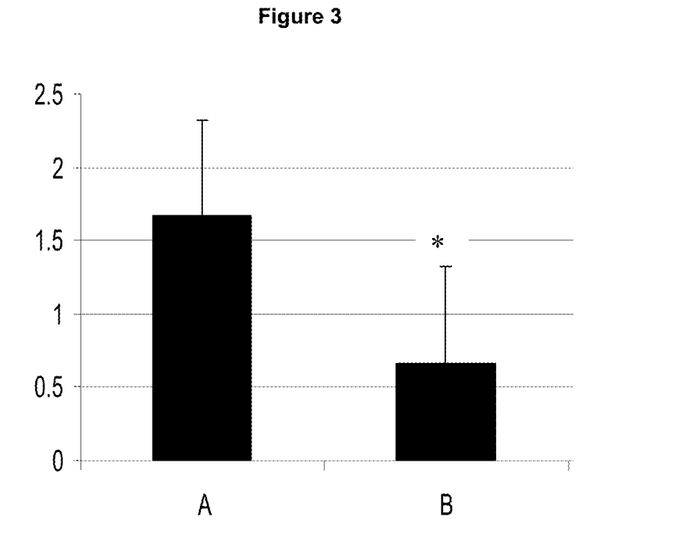
FIG. 3. Comparison of the macroscopic changes in samples of intestine of the animal group treated with BP-70+ginger and piperine additives (Group B) compared to the macroscopic changes shown by the infected but untreated control animals (Group A). The Y axis shows the score of the macroscopic changes of each group. * indicates statistically significant differences compared to the control group ($p<0.05$). BP-70: sodium butyrate (60% of the wet weight) protected with plant oil (30% of the wet weight). The percentage of ginger and piperine included in the additive was 10% of the wet weight of the total product, that is 5% ginger and 5% piperine.
Figure 4A:
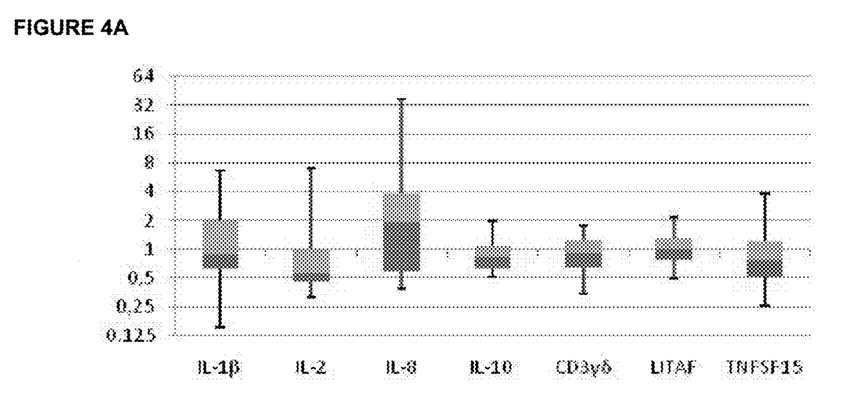
FIG. 4A shows the relative levels of expression of the genes IL-1β, IL-2, IL-8, IL-10, CD3γδ, LITAF and RNFSF15 in the groups of animals treated with BP-70 (Group C) compared to the uninfected and untreated animal group (Group A). BP-70: sodium butyrate (70% of the wet weight) protected with plant oil (30% of the wet weight). The squared area of the box spans 50% of all measurements, the horizontal line inside the box represents the mean of the sample and the vertical lines represent 50% of the measurements that were outside the values of the box. The asterisks indicate statistical significance with a value of $p<0.05$. The relative levels of gene expression indicate the expression of each gene compared to the levels of expression of each gene in Group A.
Figure 4B:
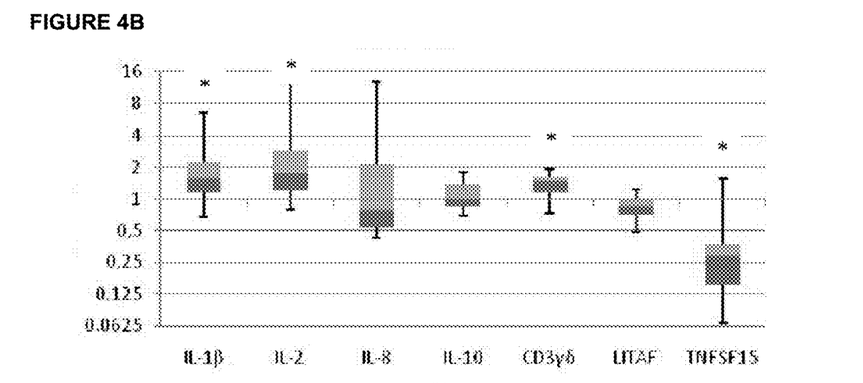
Figure 4C:
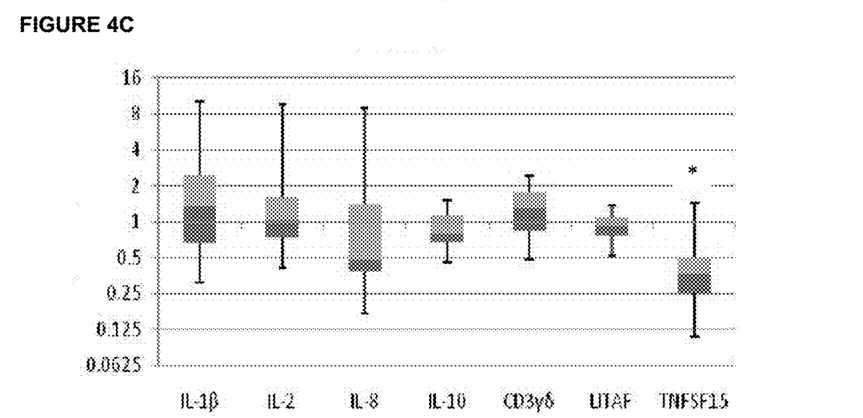
Figure 5:
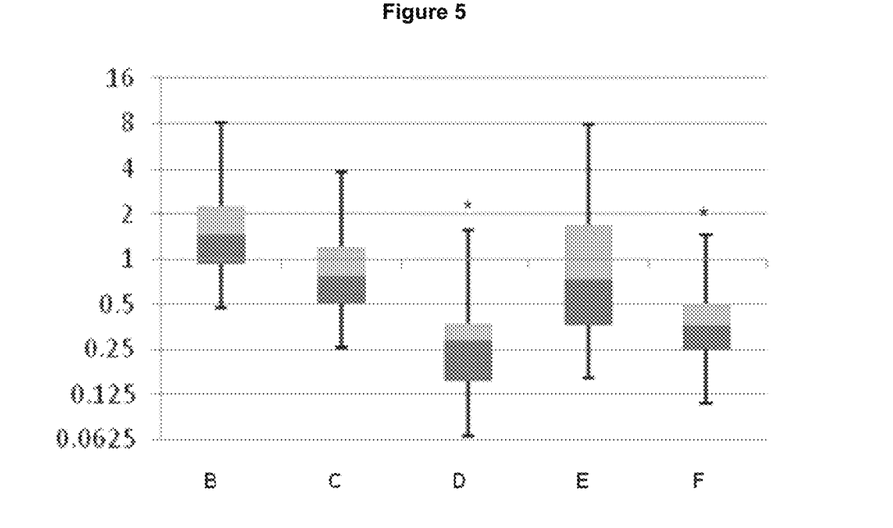
Figure 6:
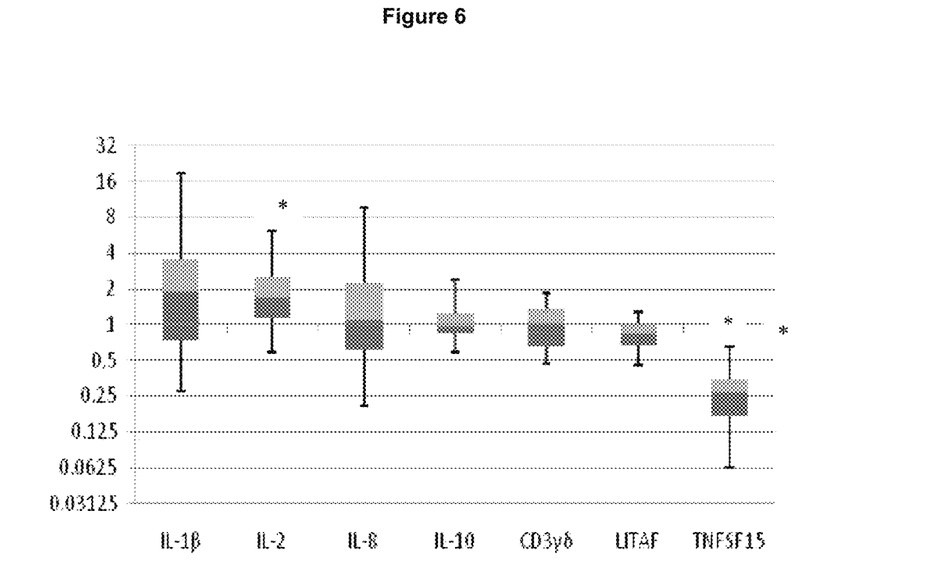
Figure 7:
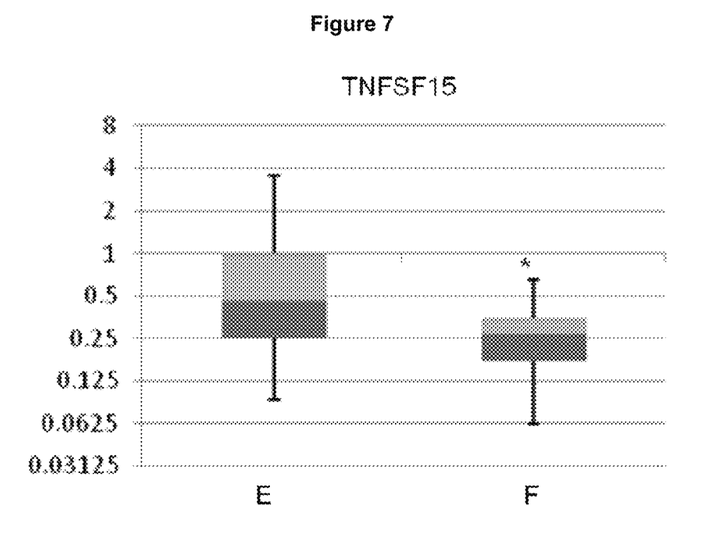

FIG. 3 shows a comparison of the severity of the macroscopic lesions seen in the group of animals treated with BP-70+ginger+piperine (Group B) compared to the control group of animals infected but not treated with any additive. As shown in FIG. 3, Group B (BP-70+ginger+piperine) showed significantly lower scores than the control group (p=0.001). Therefore, these results demonstrate that treatment with BP-70+ginger+piperine (Group B) significantly reduced macroscopic legions found in broiler chickens infected with C. perfringens A compared to control animals that showed infection but were not administrated with any type of additive (Group A).

Thus the present example demonstrates that treatment with the feed additive described in the present invention, sodium butyrate and plant essential oils, ginger and piperine, together partially coated with vegetable fats, produces a significant increase in the weight of the animals with artificial necrotic enteritis induced by inoculation with *C. perfringens A* and treated with this additive (Group B) compared to the control animal group, which also showed signs of infection but were not treated with this additive (Group A). This example also demonstrates the improvement in the lesions, mainly intestinal (caused by infection with *C. perfringens A*), that the samples extracted from the group of animals treated with the additive of the invention (Group B) showed compared to the control animal group that were not treated with any additive (Group A).

Example 2. Determination of the Immune Response of Gut-associated Lymphoid Tissue (GALT) in Broiler Chickens Suffering from Necrotic Enteritis and Treated with Various Feed Additives In order to determine the immune response of the GALT, another experimental trial was carried out with broiler chickens (n=48) that were divided into six groups (6 animals/group, Table 3). All the birds, similarly to Example 1, were treated with vaccines of Gumboro and Paracox-5® on all the days indicated in Table 1. The groups A, C and D were composed of broiler chickens not infected with *C. perfringens A*, whereas groups B, E and F were composed of broiler chickens orally infected with *C. perfringens A* (6-8×$10^8$ CFU). The base diet of the animals was the same as described in Example 1, but complemented with various additives for feed: (i) 1.5 g of BP-70/kg. of feed (Groups C and E), (ii) 1.5 g of BP-70+ginger+piperine/kg feed (Groups D and F). All the additives for feed were supplied by Norel, SA (Madrid, Spain).

TABLE 3

Experimental design

| Group | BP-70 (g/kg feed) | BP-70 + ginger + piperine: (g/kg feed) | Paracox-5 ® vaccine | Gumboro vaccine | *Clostridium perfringens* A |
|---|---|---|---|---|---|
| A | — | — | + | + | − |
| B | — | — | + | + | + |
| C | 1.5 g/kg | — | + | + | − |
| D | — | 1.5 g/kg | + | + | − |
| E | 1.5 g/kg | — | + | + | + |
| F | — | 1.5 g/kg | + | + | + |

The chickens were sacrificed on day 22 and intestinal samples were taken of approximately 5 cm length of the jejunum between Meckel's diverticulum and the iliac region. The intestinal sections were cut longitudinally and were washed three times with iced PBS containing 100 U/ml penicillin and 100 μg/ml streptomycin (Fischer Scientific). The mucous layer was scraped with a sterile glass slide and the intestinal tissue was immediately submerged in 1 ml ice cold TRizol (Invitrogen) for subsequent extraction of RNA according to the manufacturers instructions. The samples were homogenised and maintained at −80° C. until processing.

In order to evaluate the inflammatory and immune response after inducing infection with necrotic enteritis in the animals and comparing the effects of each of the treatments with the various additives described in Table 3, the changes in the levels of expression of various cytokines was evaluated by the technique of quantitative PCR (qRT-PCT). The cytokines analysed were: interleukin-1 beta (IL-1β), interleukin-2 (IL-2), interleukin-8 (IL-8), interleukin-10 (IL-10), CD3γδ receptor, lipopolysaccharide-induced tumour necrosis factor-alpha factor (LITAF) and factor 15 of the super-family of the tumour necrosis factor (TNFSF15). The control genes used as reference were: glyceraldehyde-3-phosphate dehydrogenase (GAPDH) and β-actin. The primers used for each of the genes mentioned are shown in Table 4. The interleukins-1, 2, 8 and 10 are members of the interleukin family, essential for the cellular and humoral immune response. The CD3 receptor (cluster of differentiation 3) is a target receptor found in all T-cells, LITAF is a cytokine of the TNF family that is released after LPS induction and TNFSF15 is present in endothelial cells and also participates in proliferation, differentiation and apoptosis of the cells of the immune system.

In order to analyse significant differences shown by each of the treatment groups described above in the levels of expression of the genes analysed, the ANOVA test was used.

TABLE 4

Primers used in the qRT-PCT technique

| RNA Gene | Primers Direct | Primers Inverse | Product size (bp) | GenBank Accession No. |
|---|---|---|---|---|
| GAPDH | SEQ ID No. 1 | SEQ ID No. 2 | 264 | NM_204305 |
| β-actin | SEQ ID No. 3 | SEQ ID No. 4 | 169 | NM_205518 |
| IL-1β | SEQ ID No. 5 | SEQ ID No. 6 | 80 | NM_204524 |
| IL-2 | SEQ ID No. 7 | SEQ ID No. 8 | 148 | NM_204153 |
| IL-8 | SEQ ID No. 9 | SEQ ID No. 10 | 200 | NM_205498 |
| IL-10 | SEQ ID No. 11 | SEQ ID No. 12 | 94 | NM_001004414 |
| CD3γδ | SEQ ID No. 13 | SEQ ID No. 14 | 166 | NM_205512.1 |
| LITAF | SEQ ID No. 15 | SEQ ID No. 16 | 229 | NM_204267 |
| TNFSF15 | SEQ ID No. 17 | SEQ ID No. 18 | 292 | NM_001024578 |

In order to demonstrate the immunomodulator effects provided by the feed additives administered to the various animal groups described in the present example, either infected or not with *C. perfringens*, animal Groups C and D that were treated with some of the additives mentioned and that did not show infection were compared to the untreated and uninfected control group of animals (Group A). Also, the animal groups E and F that were treated with the additives BP-70 or BP-70)+ginger+piperine respectively and that showed necrotic enteritis were compared against the group of animals infected with *C. perfringens* but not treated with any additive of those described in the present invention (Group B).

Firstly, the levels of expression of the cytokines analysed in the untreated control group of animals that were not infected with *C. perfringens* A (Group A) were compared to the groups of animals not infected with *C. perfringens* A but treated with the feed additives BP-70 (Group C) and BP-70+ginger+piperine (Group D) to analyse the natural immunomodulator effects of these additives.

FIGS. 4A, B and C show the immunomodulator effect of the additives: BP-70 and BP-70+ginger+piperine on the level of expression of the genes IL-1β, IL-2, IL-8, IL-10, CD3γδ, LITAF and TNFSF15. The relative expression ratios of these genes in the treated groups C and E were compared to those in untreated animals (Group A). None of the groups were infected with *C. perfringens* A. FIG. 4A shows that treatment with BP-70 (Group C) did not cause any change in the expression levels of the genes analysed. The major changes in the expression profile of the genes analysed occurred due to the treatment with the additive BP-70+ginger+piperine (Group D) (FIG. 4B). Three of the genes investigated were over expressed in the group of animals taking BP-70+ginger+piperine (Group D) compared to the untreated control group of animals (Group A). These genes were: IL-1β ($p=0.028$), IL-2 ($p=0.026$) and CD3γδ ($p=0.011$). One of the genes analysed, TNFSF15, showed underexpression ($p=0.004$). This underexpression was also reproduced (FIG. 4C) when comparing the untreated and uninfected control group of animals (Group A) to the infected group of animals treated with the additive described in the present invention, BP-70+ginger+piperine (Group F). Overexpression of the genes IL-1β and IL-2 indicates the activation of the immune response cascade, giving rise to stimulation of proliferation and maturation of lymphocytes. These observations were confirmed by the increase in gene expression of CD3γδ that represents a raised total T-cell count.

FIG. 5 also shows the levels of expression of each of the cytokines analysed: IL-1β, IL-2, IL-8, IL-10, CD3γδ, LITAF and TNFSF15, in each of the groups of animals treated with each of the additives described in the present example and that were either infected or not with *C. perfringens A* (Groups C to F), as well as the control group of animals infected with *C. perfringens A*, but not treated with any of these additives (Group B). FIG. 5 demonstrates that treatment with BP-70+ginger+piperine (Group E) caused underexpression of the gene TNFSF15 compared to both the control and uninfected group of animals that were not given any additive in their diet (Group A) and in the infected group of animals that were also not given any additive in their diet (Group B).

Secondly, the immunomodulator effects provided by feed additives given to animals of the groups E (BP-70) and F (BP-70+ginger+piperine), treated with the additives mentioned and that had necrotic enteritis, were analysed with respect to the group of animals infected with *C. perfringens* but not treated with any additive of those described in the present invention (Group B).

FIG. 6 shows the levels of expression of the genes IL-1β, IL-2, IL-8, IL-10, CD3γδ, LITAF and TNFSF15 in the group of animals infected with *C. perfringens A* and that were treated with the feed additive described in the present invention, BP-70+ginger+piperine (Group F), compared to the levels of expression of these genes in the group of control animals infected with *C. perfringens A* but that were not fed with the additives used in the present example (Group B). This analysis was carried out to analyse the effects of these additives in the evolution of the infection. FIG. 6 shows that there was a significant increase in the levels of expression of cytokine IL-2 compared to the control untreated group (Group B). Furthermore, the group of animals treated with BP-70+ginger+piperine showed a decrease in the levels of expression of TNFSF15 compared to the untreated control group of animals (Group B).

Similarly, FIG. 7 shows the level of expression of cytokine TNFSF15 in the group of animals infected and treated with BP-70+ginger+piperine (Group F) compared to the control group of animals that were infected but not treated (Group B). Treatment with BP-70+ginger+piperine (Group F) caused underexpression of TNFSF15 compared to the control group (Group B).

In accordance with the results shown in the present example, treatment with sodium butyrate+essential oils, exemplified in the present invention by treatment with BP-70+ginger+piperine, was able to show a significant modulator action on the immune response, causing an increase in the expression of genes coding for the cytokines IL-1β, IL-2 and CD3γδ and a decrease in the expression of the gene coding for the cytokine TNFSF15, giving rise to a protector effect against artificial infection caused by *C. perfringens A.*

Furthermore, as demonstrated in the results shown in Example 1, treatment with the additive described in the present invention is also able to induce an increase in weight gain of animals subjected to this treatment and reduce the severity of histological lesions shown by these animals as a consequence of infection with *C. perfringens A.*

The invention claimed is:

1. A method for promoting animal growth comprising administering an additive to an animal, wherein said additive comprises a combination of sodium butyrate with essential oils consisting of essential oils of ginger and essential oil piperine, wherein the combination is partially coated with a palm stearin coating.

2. The method according to claim 1, wherein the sodium butyrate is in a proportion of 30-70% of the wet weight of the additive.

3. The method according to claim 1, wherein the sodium butyrate is in a proportion of 60% of the wet weight of the additive.

4. The method according to claim 1, wherein the essential oils consisting of essential oils of ginger and essential oil piperine are in a concentration of between 1-20% of the wet weight of the additive.

5. The method according to claim 1, wherein the essential oils consisting of essential oils of ginger and essential oil piperine are in a concentration of 10% of the wet weight of the additive.

6. The method according to claim 5, wherein the concentration of the essential oils of ginger is 5% wet weight of the additive and the concentration of the essential oil piperine is 5% wet weight of the additive.

7. The method according to claim 1, wherein the palm stearin coating is between 30-60% wet weight of the additive.

8. The method according to claim 1, wherein the palm stearin coating is 30% wet weight of the additive.

9. The method according to claim 1, wherein the concentration of sodium butyrate is 60% of the wet weight of the additive, the concentration of the essential oils consisting of essential oils of ginger and the essential oil piperine are 10% of the wet weight of the additive, and wherein the concentration of the palm stearin coating is 30% of the wet weight of the additive.

10. The method according to claim 9, wherein the concentration of the essential oils of ginger is 5% of the wet weight of the additive and the concentration of the essential oil piperine is 5% of the wet weight of the additive.

11. The method of claim 1, wherein the animal is selected from the group consisting of a chicken, a rabbit, and a pig.

* * * * *

SEQUENCE LISTING

```
<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct

<400> SEQUENCE: 1
```
ggtggtgcta agcgtgttat                                                    20

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct

<400> SEQUENCE: 2
acctctgtca tctctccaca                                                    20

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
gtccaccttc cagcagatgt                                                    20

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
ataaagccat gccaatctcg                                                    20

<210> SEQ ID NO 5
<211> LENGTH: 24
<212> TYPE: DNA
<213> ORGANISM: Artificial Sequence
<220> FEATURE:
<223> OTHER INFORMATION: Synthetic Construct

<400> SEQUENCE: 5
gctctacatg tcgtgtgtga tgag                                               24

<210> SEQ ID NO 6
<211> LENGTH: 18
<212> TYPE: DNA
<213> ORGANISM: Artificial Sequence
<220> FEATURE:
<223> OTHER INFORMATION: Synthetic Construct

<400> SEQUENCE: 6
tgtcgatgtc ccgcatga                                                      18

<210> SEQ ID NO 7
<211> LENGTH: 21
<212> TYPE: DNA
<213> ORGANISM: Artificial Sequence
<220> FEATURE:
<223> OTHER INFORMATION: Synthetic Construct

<400> SEQUENCE: 7
cccagcaaac tctgcagtgt t                                                  21

<210> SEQ ID NO 8
<211> LENGTH: 21
<212> TYPE: DNA
<213> ORGANISM: Artificial Sequence

```
<220> FEATURE:
<223> OTHER INFORMATION: Synthetic Construct

<400> SEQUENCE: 8
ccggtgtgat ttagacccgt a                                              21

<210> SEQ ID NO 9
<211> LENGTH: 19
<212> TYPE: DNA
<213> ORGANISM: Artificial Sequence
<220> FEATURE:
<223> OTHER INFORMATION: Synthetic Construct

<400> SEQUENCE: 9
ggcttgctag gggaaatga                                                 19

<210> SEQ ID NO 10
<211> LENGTH: 24
<212> TYPE: DNA
<213> ORGANISM: Artificial Sequence
<220> FEATURE:
<223> OTHER INFORMATION: Synthetic Construct

<400> SEQUENCE: 10
agctgactct gactaggaaa ctgt                                           24

<210> SEQ ID NO 11
<211> LENGTH: 21
<212> TYPE: DNA
<213> ORGANISM: Artificial Sequence
<220> FEATURE:
<223> OTHER INFORMATION: Synthetic Construct

<400> SEQUENCE: 11
ctttggctgc cagtctgtgt c                                              21

<210> SEQ ID NO 12
<211> LENGTH: 21
<212> TYPE: DNA
<213> ORGANISM: Artificial Sequence
<220> FEATURE:
<223> OTHER INFORMATION: Synthetic Construct

<400> SEQUENCE: 12
gctctgctga tgactggtgc t                                              21

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct

<400> SEQUENCE: 13
cagggattgt ggtcgcagat                                                20

<210> SEQ ID NO 14
<211> LENGTH: 22
<212> TYPE: DNA
<213> ORGANISM: Artificial Sequence
<220> FEATURE:
<223> OTHER INFORMATION: Synthetic Construct

<400> SEQUENCE: 14
tactgtccat cattccgctc ac                                             22
```

```
<210> SEQ ID NO 15
<211> LENGTH: 24
<212> TYPE: DNA
<213> ORGANISM: Artificial Sequence
<220> FEATURE:
<223> OTHER INFORMATION: Synthetic Construct

<400> SEQUENCE: 15
tgtgtatgtg cagcaacccg tagt                                              24

<210> SEQ ID NO 16
<211> LENGTH: 23
<212> TYPE: DNA
<213> ORGANISM: Artificial Sequence
<220> FEATURE:
<223> OTHER INFORMATION: Synthetic Construct

<400> SEQUENCE: 16
ggcattgcaa tttggacaga agt                                               23

<210> SEQ ID NO 17
<211> LENGTH: 22
<212> TYPE: DNA
<213> ORGANISM: Artificial Sequence
<220> FEATURE:
<223> OTHER INFORMATION: Synthetic Construct

<400> SEQUENCE: 17
cctgagttat tccagcaacg ca                                                22

<210> SEQ ID NO 18
<211> LENGTH: 24
<212> TYPE: DNA
<213> ORGANISM: Artificial Sequence
<220> FEATURE:
<223> OTHER INFORMATION: Synthetic Construct

<400> SEQUENCE: 18
atccaccagc ttgatgtcac taac                                              24
```